United States Patent [19]
Arndt

[11] Patent Number: 5,399,087
[45] Date of Patent: * Mar. 21, 1995

[54] NI-TI ORTHODONTIC PALATAL EXPANSION ARCH WITH CAST LINGUAL SHEATH AND INSERT

[76] Inventor: Wendell V. Arndt, 26650 W. 143rd St., Olathe, Kans. 66062

[*] Notice: The portion of the term of this patent subsequent to Dec. 1, 2009 has been disclaimed.

[21] Appl. No.: 984,381

[22] Filed: Nov. 30, 1992

Related U.S. Application Data

[63] Continuation-in-part of Ser. No. 833,536, Feb. 10, 1992, abandoned, and Ser. No. 662,204, Feb. 27, 1991, Pat. No. 5,167,499.

[51] Int. Cl.⁶ .............................................. A61C 3/00
[52] U.S. Cl. ................................... 433/7; 433/20; 433/17
[58] Field of Search ................... 433/4, 5, 7, 17, 20, 433/22

[56] References Cited

U.S. PATENT DOCUMENTS

| | | | |
|---|---|---|---|
| 1,395,922 | 11/1921 | McCarter | 433/20 |
| 1,429,749 | 9/1922 | Maeulen et al. | 433/20 |
| 1,471,785 | 6/1922 | Fernald | 433/20 |
| 1,582,570 | 3/1925 | Brust | 433/7 |
| 1,594,143 | 7/1926 | Angle et al. | 433/4 |
| 3,477,129 | 11/1969 | Rubin | 433/17 |
| 4,412,819 | 11/1983 | Cannon | 433/20 |
| 4,479,779 | 10/1984 | Wool | 433/20 |
| 4,571,179 | 2/1986 | Balenseifen | 433/20 |
| 4,592,725 | 6/1986 | Goshgarian | 433/7 |
| 4,669,980 | 6/1987 | Degnan | 433/17 |
| 4,815,968 | 3/1989 | Keller | 433/7 |
| 4,818,226 | 4/1989 | Berendt et al. | 433/20 |
| 4,854,864 | 8/1989 | Cleary | 433/7 |
| 4,897,035 | 1/1990 | Green | 433/17 |
| 4,900,251 | 2/1990 | Andreasen | 433/20 |
| 4,976,614 | 12/1990 | Tepper | 433/20 |
| 5,007,828 | 4/1991 | Rosenberg | 433/7 |

FOREIGN PATENT DOCUMENTS 525429  4/1931  Germany ............................ 433/17

OTHER PUBLICATIONS

Ronald A. Bell, D.D.S., M.D., *A review of maxillary expansion in relation to rate of expansion and patient's age*, Jan., 1982, pp. 32–37.

Oscar E. Muguerza, D.D.S., M.S.D., and Peter A. Shapiro, D.D.S., M.S.D., *Palatal mucoperiostomy: An attempt to reduce relapse after slow maxillary expansion*, Nov., 1980, pp. 548–558.

E. Preston Hicks, D.D.S., M.S.D., *Slow maxillary expansion (A clinical study of the skeletal versus dental response to low–magnitude force)*, Feb., 1978, pp. 121–141.

A. J. Haas, D.D.S., M.S., *Long-Term Posttreatment Evaluation of Rapid Palatal Expansion*, Jul., 1980, pp. 189–219.

*Primary Examiner*—Cary E. O'Connor
*Attorney, Agent, or Firm*—Richard P. Stitt

[57] ABSTRACT

An orthodontic expansion arch and sheath and sheath insert are provided for use in applying maxillary and mandibular lingual orthodontic appliances for expansion of the arches. The sheath permits use of appliances employing multiple wires composed of non-weldable metal alloys in a more convenient manner and in a greater variety of appliances.

30 Claims, 8 Drawing Sheets

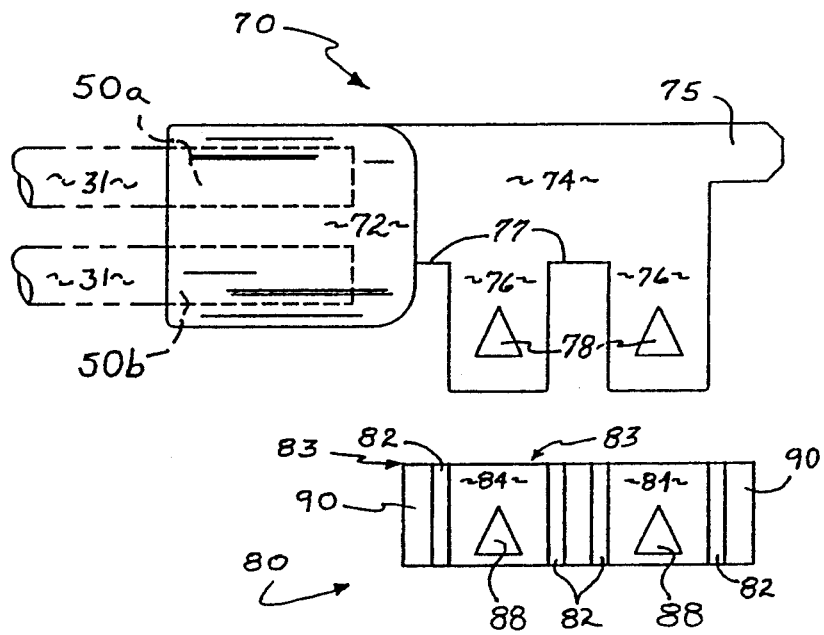
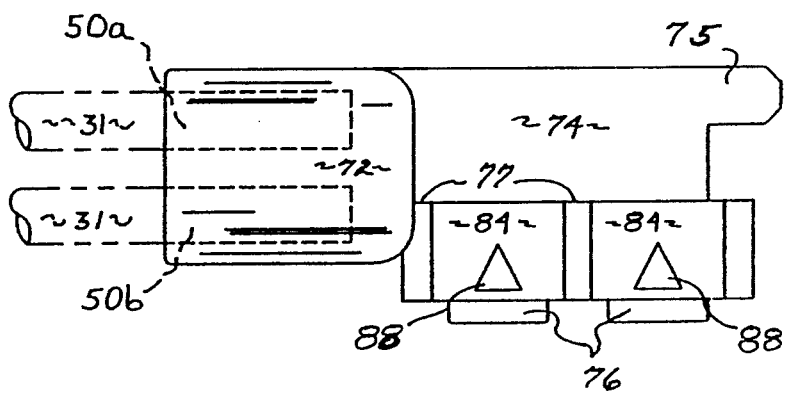
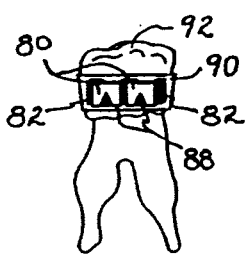
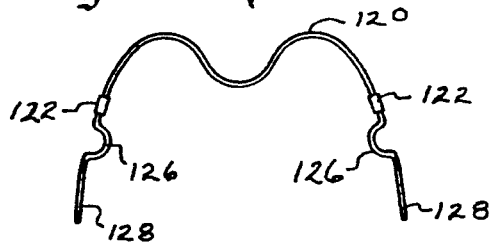
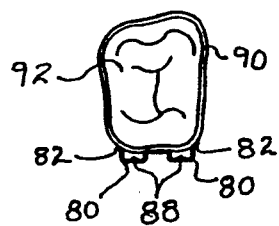
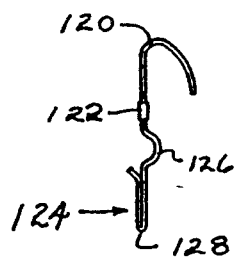

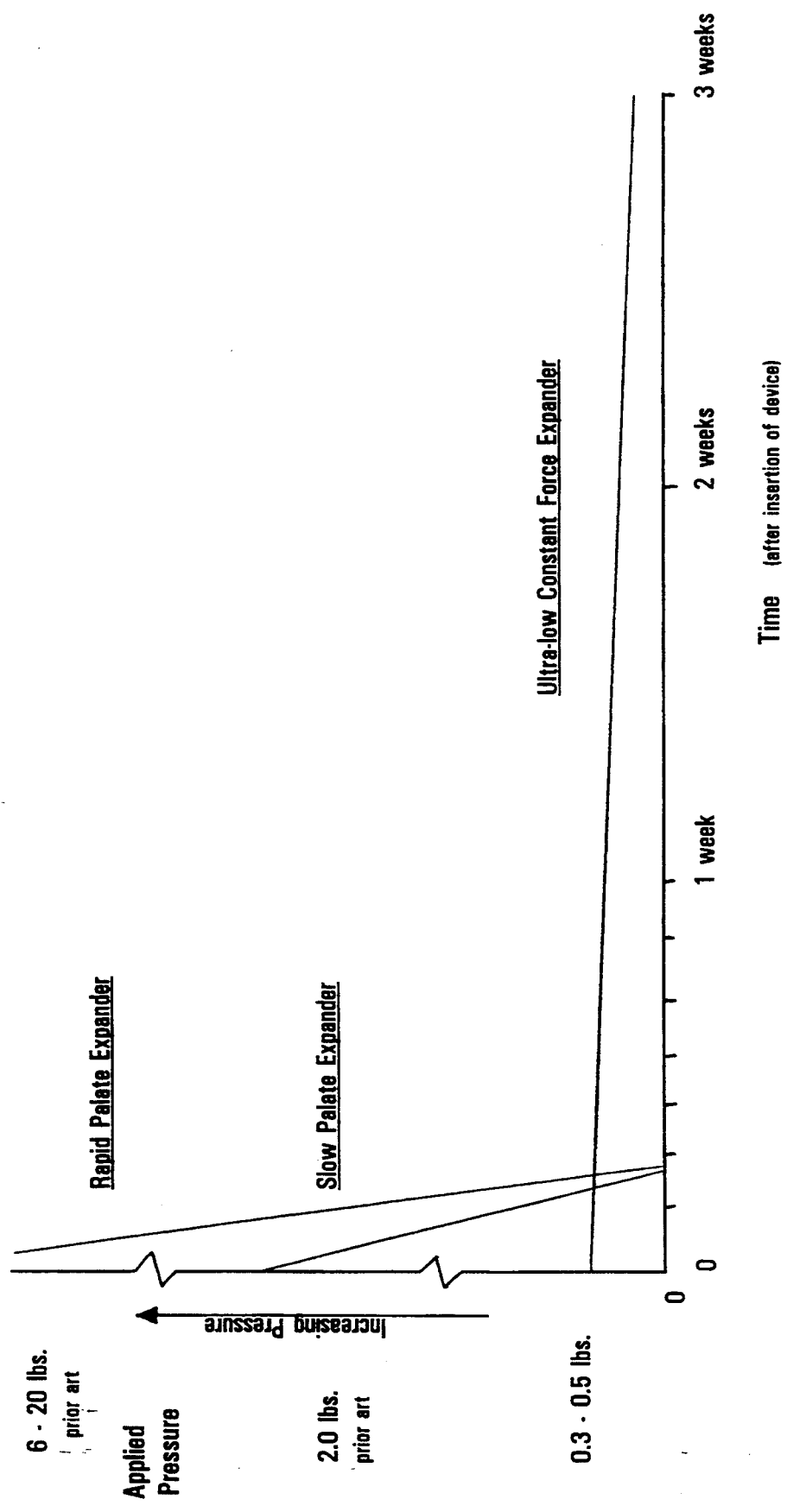

NI-TI ORTHODONTIC PALATAL EXPANSION ARCH WITH CAST LINGUAL SHEATH AND INSERT

This is a continuation-in-part of application Ser. No. 07/662,204, filed on Feb. 27, 1991, and issued at U.S. Pat. No. 5,167,499, and a continuation-in-part of application Ser. No. 07/833,536, filed on Feb. 10, 1992, now abandoned.

FIELD OF THE INVENTION

The invention relates generally to the field of orthodontic appliances. More particularly, to an orthodontic appliance for spreading the palatal arch and an adapter for securing orthodontic appliances within the mouth and, with further particularity, appliances employing nickel-titanium alloys for moving and positioning teeth.

BACKGROUND OF THE INVENTION

The dental specialty orthodontics is concerned with the correction of alignment and positional abnormalities of the teeth. It is not uncommon for patients receiving such treatment to require a regimen which continues over many months and involves the use of various appliances affixed within the mouth to achieve repositioning of displaced teeth. The repositioning is accomplished, generally, by attachment of an orthodontic appliance to one or several of the teeth in order to provide forces on the affected teeth which accomplish the desired repositioning.

Often it is necessary for the orthodontic clinician to reposition a patient's maxillary and mandibular first permanent molars by de-rotating the molars or expanding the distance between the molars. This procedure, in the case of maxillary first permanent molars, is often accomplished during the course of generally expanding the palate to properly position the molars and reduce crowding of the upper arch interior teeth as well as to adjust the occlusion and bite.

To achieve this expansion of the molars and the palatal arch it has been common practice to utilize various types of arch bars or jack screws which are positioned between the maxillary molars to achieve rotation of the molars and to accomplish the desired expansion of the palate.

Typically these types of devices require a number of weeks or months of action on the teeth to accomplish the desired goal. In the case of stainless steel type arch wires the orthodontic appliance operates by simple mechanical pressure against the lingual side of the molars. The stainless steel appliance's ability to expand the palate is limited to the steel's capacity to withstand compression before reaching its yield point. This limitation of stainless steel requires periodic return visits to the orthodontist so the appliance can be reformed.

This periodic reforming of the appliance is necessary to restore the desired moment-of-force applied by the device and to realign the direction of force application with respect to the teeth. This is accomplished by modifying the shape of the appliance. This shape modification is necessary as often the stainless steel appliance must be initially bent into incorrect alignments to permit affixation to the mispositioned teeth.

Usually, the tooth repositioning process with stainless steel involves the incorporation of U-shaped bends into the arch which are slowly expanded over weeks to maintain force on the teeth and to increase the distance of separation between the molars. Such treatment requires multiple appointments with the orthodontic clinician and removal of the arch wire from the patient followed by reshaping of the device and reinstallation. This procedure can be time consuming and require substantial patient chair time.

In the case of jack-screw type palatal expansion devices, the expansion screw is affixed to the molars and over a period of several weeks the teeth are expanded by having the patient lengthen the screw by quarter turn increments on a daily basis. This type of device requires patient involvement in the treatment. Patient involvement may be improperly attended to or not conducted at all. In addition, patient manipulation of the device can result in damage to the appliance or injury to the patient. The vagaries of patent involvement are best avoided for most efficient results.

More importantly, such jack-screw type devices operate by the initial application of forces in the range of hundreds of grams. Forces on the order of 500 to 1300 grams are initially applied to the teeth when the jack screw is manipulated in the clinician's office. This initial high force application to the teeth is then followed by rapid movement of the teeth and a nearly immediate decay of the force to a pressure of zero. Such intermittent high force is considered, by orthodontic researchers, to be almost detrimental to the overall result and is suspected of resulting in retrograde bone destruction.

Recently, the introduction of improved metal alloys to the art of orthodontic appliance manufacture has resulted in the ability to provide palatal arch expansion devices and other orthodontic appliances which can apply force to the teeth over a much greater range of distances. Previously, with stainless steel type devices, the range of motion of the orthodontic appliance was limited by the distance over which stainless steel could be compressed and still maintain its tendency to spring back to its original shape. As the capacity of stainless steel to be bent or compressed without yielding is limited, multiple patient visits were required to accomplish the desired movement of teeth over the full distance to achieve proper positioning.

This limitation of stainless steel has been overcome by the use of metal alloys which present a "shape memory" which allows the orthodontic appliance to be bent and twisted to a much greater extent than a stainless steel device without resulting in a permanent reconfiguration of the device.

One such type of alloy is the nickel-titanium (Ni—Ti) alloy combinations, generally known as Nitinol, and is sold commercially under the trademark "Tinel" by Raychem Corp. of Menlo Park, Calif. Nitinol alloy is a known near-stoichiometric alloy of nickel and titanium. The alloy may also include cobalt substituted for nickel on an atom-for-atom basis so that the composition is Ni—Ti; Co: 0.935, 0.065.

Nickel-titanium alloy metals offer unique physical characteristics. Of particular interest in the field of orthodontics is the property of conformation or shape memory of the metal. That is, the alloy presents temperature dependent flexibility properties and strength properties which can be utilized to particular advantage in orthodontic appliances. Such nickel-titanium alloys present two types of physical states, the transition between which is temperature activated. The particular temperature at which the metal shifts from one state to another is dependent upon the contents of the alloy. At temperatures below the transition temperature the metal is in its "martensitic" state. In this state the metal is comparatively soft and may be deformed and twisted with relative ease. This property of the alloy is of particular utility in orthodontics for the metal, when in its martensitic state, may be twisted and greatly distorted without surpassing the metals yield point which would result in permanent conformation changes. Thus, this property permits the orthodontic clinician to bend and twist the orthodontic appliance during the application session without damaging the appliance.

As utilized in orthodontic appliances these metal alloys provide corrective force by taking advantage of the body temperature of the patient to provide the transition temperature of the particular metal alloy composition. When the metal is at a temperature above the transition temperature it is said to be in its "austenitic" state within which the metal seeks to return to a predetermined shape. It is this property of reverting to an original conformation at temperatures above the transition temperature which provides the forces useful in orthodontic appliances. The properties of Nitinol permit the application of low forces to orthodontic applications and forces which are substantially consistent over the range of motion as the appliance moves back into its original or "memory" shape.

However, nickel-titanium and similar alloys present the limitation in that welding the metal is not possible. The heat of welding will result in modification or destruction of the "memory" conformation. Therefore, to accomplish attachment of the Nitinol orthodontic device to the teeth, it is necessary to use a crimp tube adapter to join a second workable metal to the Nitinol. An example of such a prior art method of securing a Nitinol arch is illustrated in FIGS. 10 and 11.

Such tube crimp connectors inhibit the joining of more than one Ni—Ti wire to another Ni—Ti wire or to a sheath insert or end piece. If the clinician desires to use multiple Ni—Ti wires in a treatment, several such crimp tubes must be soldered together, either one atop the other or some other arrangement, to permit the use of multiple Ni—Ti segments in the appliance. This results in an expensive and cumbersome device and one which presents increased opportunity for breakage with each soldered connection.

Objects of the Invention

Therefore it is an object of the present invention to provide an adapter for joining non-weldable orthodontic appliance materials directly to a sheath insert.

Yet another object of the invention is to provide a device for releasably securing a lingual arch or other orthodontic appliance within a lingual sheath.

Another object of the present invention is to provide a device for joining multiple nickel-titanium lingual arch wires together and for joining multiple arch wires within a sheath insert.

Another object of the present invention is to provide a sheath insert which is removable.

Still another object of the present invention is to provide a sheath and sheath insert which are not easily separable by the patient.

Yet another object of the present invention is to provide a sheath and sheath insert which permit the use of small diameter nickel-titanium wires for use in orthodontic appliances for younger children.

Another object of the present invention is to provide a sheath and sheath insert which also act as a joining device for multiple arch wires.

Yet another object of the present invention is to provide a sheath insert which may be selectably modified by the orthodontic clinician to provide increased variation of directional forces utilized in the repositioning of teeth and in palatal arch expansion.

Another object of the present invention is to provide a sheath and sheath insert having redundant safety features to prevent patient dislodgement.

Yet another object of the present invention is to provide a sheath and sheath insert which have registrable indents to assist in removably locking the sheath insert within the sheath.

Another object of the present invention is to provide a sheath and sheath insert offering attachment points for orthodontic elastomers and for soldering lock-wires thereto.

Another object of the present invention is to reduce the chair time for patient care over prior art devices.

Still another object of the present invention is to provide a vertical sheath and vertical sheath insert which avoids the tendency of prior art devices to be removed by the patient.

Yet another object of the present invention is to provide a palatal expansion arch with memory-retaining characteristics capable of expanding the palate bilaterally and thus providing more space for the anterior teeth to assume their proper position in the maxillary arch.

Another object of the present invention is to provide a palatal expansion arch which is capable of providing palate expanding forces to expand the bicuspids and rotate, expand, intrude, and/or torque the molars.

Still another object of the invention is to provide a palatal expansion arch that provides low constant mechanical forces at ambient and below mouth temperatures and applies a greater sustained constant force when at mouth temperature through treatment until the desired change in palatal width and molar rotation is achieved.

Still another object of the invention is to provide a palatal expansion orthodontic appliance capable of delivering a constant, soft, uniform pressure or movement of teeth and to provide proper bone plating at the palatal suture.

It is another object of the present invention to provide a palatal expansion arch capable of varying the load intermittently which is applied to the teeth.

It is another object of the present invention to provide a palatal expansion arch which permits patient selectable cessation or activation of the forces applied to the patient's teeth.

These and other objects are not meant in a limiting sense and will be pointed out and described in further detail hereinafter.

BRIEF DESCRIPTION OF THE DRAWINGS

FIG. 5 is a side elevational view of an alternative embodiment of the invention showing a vertical sheath with a vertical sheath insert oriented for positioning within the vertical sheath;

FIG. 6 is a side elevational view of the embodiment of FIG. 5 showing the vertical sheath insert within the vertical sheath;

FIG. 7 is a side perspective view of the vertical sheath attached to a band on a molar;

FIG. 8 is a plan view of the vertical sheath of FIG. 7 and showing the band encompassing the molar;

FIG. 9 is a plan view of an arch wire connected to a prior art horizontal sheath insert by crimp tubes;

FIG. 10 is a side view of the arch wire and sheath insert of FIG. 9 showing the doubled over "U-shaped" end portion for insertion into a sheath;

FIG. 33 shows a comparison of the pressure decay of prior art stainless steel devices with shape memory-retaining devices

DETAILED DESCRIPTION OF THE PREFERRED EMBODIMENTS

Figure 1:
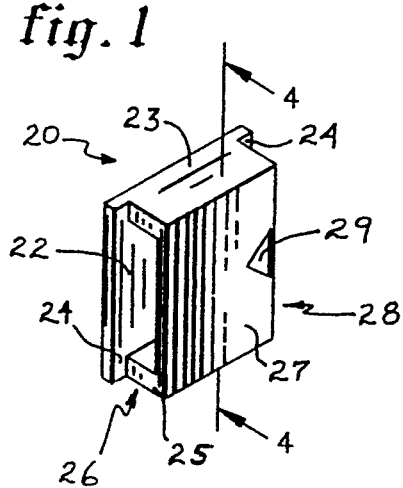
FIG. 1 is a perspective view of the horizontal lingual sheath and showing the sheath indent.
Figure 2:
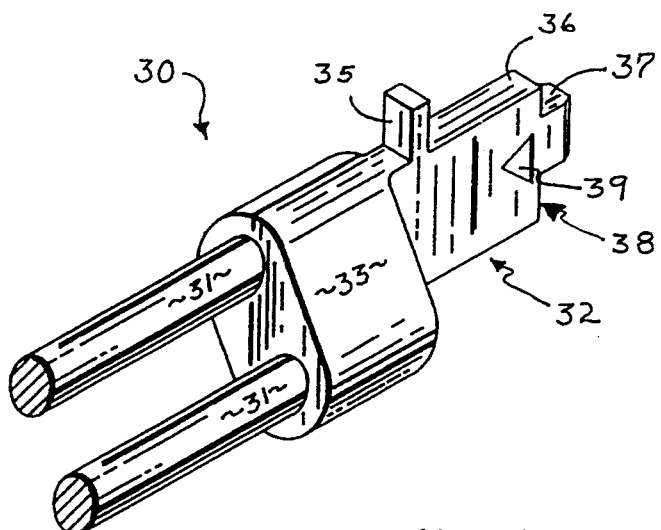
FIG. 2 is a perspective view of the horizontal lingual sheath insert showing the inserted arch wires of an orthodontic appliance.

In FIG. 1 is illustrated horizontal sheath 20 of the present invention and in FIG. 2 is illustrated horizontal sheath insert 30 for capture by sheath 20. Sheath 20 is provided with back portion 22 having flanges 24 to permit attachment of sheath 20 to a stainless steel band placed about a tooth or molar. Such a band 90 is shown in FIGS. 6 and 7, but illustrating the connection of an alternative sheath embodiment.

Sheath 20 of FIG. 1 is a horizontal-insert type of sheath and is positioned within the mouth such that anterior end 26 of sheath 20 is oriented towards the front of the mouth while posterior end 28 is oriented towards the back or posterior of the mouth. This orientation is such that indent 29 on lingual wall 27 is positioned at the posterior of the sheath. While sheath 20 and sheath insert 30 are usually composed of cast stainless steel, other alloys commonly employed in such orthodontic appliances are equally acceptable. Lingual wall 27 is attached to back wall 22 by sides 23, 25. The dimensions of sheath 20 are such that a frictional fit is provided with sheath insert 30.

Figure 3:
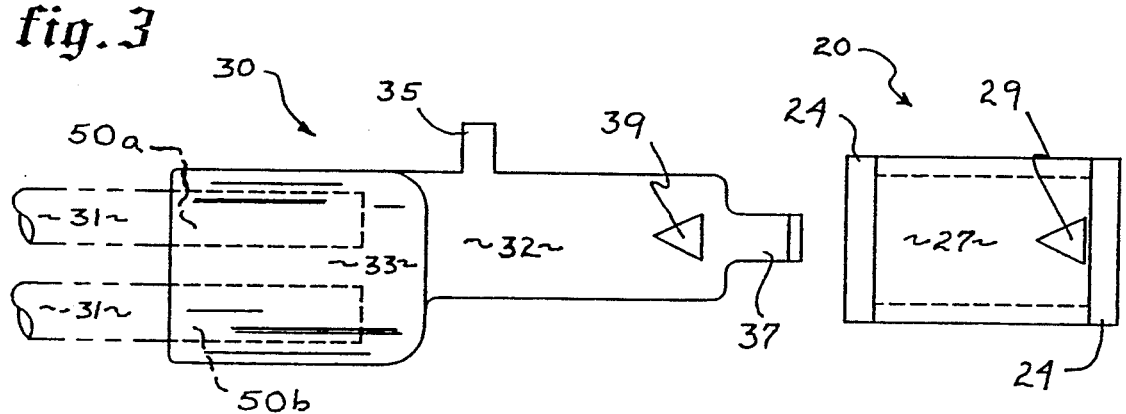
FIG. 3 is a side elevational view of the lingual sheath and lingual sheath insert and showing in phantom lines the appliance insert cavities and the extending stop.

Horizontal sheath insert 30 is illustrated in FIG. 2 and is shown with partially illustrated arch wires 31 of an orthodontic appliance inserted into cavities 50A, 50B (FIG. 3). Sheath insert 30 is composed of cast stainless steel or other suitable material for use in the mouth. Insert 30 may be subdivided, for purposes of discussion, into two general portions; sheath insert or post portion 32 and appliance reception or securing member portion 33. Appliance reception portion 33 may be altered according to the requirements and shape of the particular appliance. Sheath insert portion 32, however, is maintained in standard dimensions and conformation. In this manner sheath 20, once installed in a patient's mouth, may be utilized with a variety of orthodontic appliances where clinically efficacious.

Extension 35 projects from edge 36 of insert post portion 32. Extension 35 provides two functions, it serves as a positive stop when insert 30 is placed into sheath 20, and can act as an securing post for an elastomer or soldered wire lock. Extension 35 operates as a positive stop by contacting anterior end 26 of side 23 as sheath insert portion 32 is captured by sheath 20. This provides a positive stop on the rearward movement of sheath insert 30 during insertion into sheath 20. In addition, extension 35 offers added stability to sheath insert 30 and sheath 20 when in contact with one another.

For service as a point of attachment for an elastomer or soldered wire lock, extension 35 projects slightly above the anterior edge of side 23. Thus extension 35 may be useful in locking the sheath insert 30 into sheath 20 by application of an elastomer between extension 35 and arm 37. For more permanent locking of the sheath insert 30 into sheath 20, a wire may be soldered to extension 35 and to arm 37 to prevent release of the orthodontic appliance.

Extending from posterior end 38 of sheath insert portion 32 is arm 37. Arm 37 also extends rearwardly from posterior end 28 of sheath 20 when sheath insert 30 is seated within sheath 20. This relationship may be observed in FIG. 4. As described above, arm 37 provides a second point of attachment for an orthodontic elastomer or for soldered a wire lock.

As an alternative to connecting an orthodontic elastomer between extension 35 and arm 37, the elastomer may be attached to the orthodontic appliance held within appliance reception portion 33 and then extended rearwardly and attached to arm 37.

Appliance reception portion 33 of sheath insert 30 may be cast simultaneously with sheath insert portion 32 to present the final conformation of appliance reception portion 33. Alternatively, appliance reception portion 33 may be cast as blocks of material, variously sized, for later shaping and drilling to accommodate the particular orthodontic appliance of choice for attachment to the sheath insert by the clinician.

While the sheath and the sheath insert of the present invention may be utilized with a wide range of orthodontic appliances made from a full range of materials, the inventive sheath and sheath insert are of particular utility for use in conjunction with metal alloys which, due to their particular properties, may not be welded. Rather the formation of the appliance requires use of various "crimp tube" connectors to form the appliance and/or to join a sheath insert thereto to permit affixation within the mouth. In FIG. 9 nickel-titanium alloy arch 120 is joined to crimp tube 122. Attached to the other end of crimp tube 122 is adapter 124. Adapter 124 also contains adjustment loop 126 which may be utilized to lengthen or shorten the adapter 124 to correct for patient variations. Referring now to FIG. 10 a side elevational view of FIG. 9 is illustrated. A double-backed portion or U-shaped portion 128 of adapter 124 is shown and is the commonly utilized insert adapter of the prior art.

Figure 4:
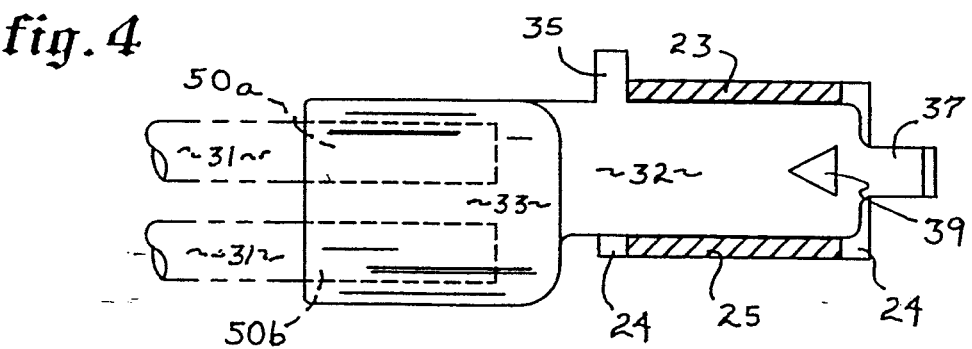
FIG. 4 is a cross-sectional view of the sheath taken along line 4—4 of FIG. 1 and showing in side elevational view the sheath insert positioned within the sheath.

Referring now to FIG. 3, the pre-insertion alignment of sheath insert 30 and sheath 20 is illustrated in side elevational view. In FIG. 4 the sheath insert 30 has been placed into sheath 20 and the abutting of extension 35 against side 23 to provide a positive stop to insertion can be observed. By examining FIG. 3 in combination with FIG. 4 the operation indent 29 on sheath 20 and indent 39 on insert 30 may be discussed.

As shown in FIG. 4 when insert 30 is inserted in sheath 20, indent 39 on insert portion 32 is thrust towards the posterior end 28 of sheath 20 and will come into registration with indent 29 on sheath 20 as an extension 35 contacts side 23 of sheath 20. Indent 29 of sheath 20 causes a portion of wall 27 to protrude inwardly and toward back wall 22 of sheath 20. This protrusion into the interior of sheath 20 and the close registration between sheath insert 30 and sheath 20 causes protruding indent 29 to be inserted into indent 39 when sheath insert portion 32 is seated within sheath 20. This close registration provides a positive, but releasable lock of sheath insert 30 within sheath 20. This positive lock assists in preventing inadvertent patient removal of the appliance as the tongue contacts the appliance and pushes it forward.

As may be observed in FIG. 4 arm 37 extends from the posterior 28 of sheath 20. This extension of arm 37 beyond sheath 20 provides a point of attachment for an orthodontic elastomer having its other end attached to the orthodontic appliance 31. Alternatively, if it is desired to more permanently attach the appliance, a piece of wire rather than an elastomer may be soldered between arm 37 and extension 35. Thus permanent capture of the sheath insert 30 within sheath 20 is accomplished.

Referring now to FIG. 5 an alternative embodiment of the sheath and sheath insert is illustrated. The embodiment of FIG. 5 is in the vertical sheath and vertical insert configuration. This name is indicative of the nearly vertical direction of insertion of insert 70 into sheath 80.

Sheath insert 70 may again, for purposes of discussion, be divided into two portions; an appliance reception portion 72 and a sheath insert portion 74. As was the case with the horizontal sheath insert, appliance reception portion 72 of vertical insert 70 is preferably cast in a unitary manner with sheath insert portion 74. At the time of casting, appliance reception portion 72 may be precisely shaped for the intended orthodontic appliance, or alternatively, appliance reception portion 72 may be cast as a generally defined block of material for later drilling and shaping. In this manner the clinician may use the sheath insert and sheath with the available manufactured orthodontic appliances or the clinician may choose to modify appliance reception portion 72 for use with a custom orthodontic appliance. In the embodiment illustrated in FIG. 5 the appliance reception portion 72 has been pre-drilled to include appliance cavities 50A, 50B.

Sheath insert portion 74 is provided with insertion posts 76 which are sized for complemental reception in sleeves 84 of sheath 80. Again, as in the horizontal sheath and sheath insert embodiment, the vertical sheath and sheath insert embodiment is provided with indent 78 on sheath insert posts 76 and indent 88 on sleeves 84 of sheath 80. When sheath insert 70 is pressed into sheath 80 indent 88 of sheath 80 registers with indent 78 on post 76 to provide a frictional locking of vertical insert 70 within vertical sheath 80. It should be appreciated that as vertical insert 70 contacts vertical sheath 80, stops 77 at the lower edge of the main body of sheath insert portion 74, contact upper edge 83 of sheath 80 to provide a positive contact between insert 70 and sheath 80 to provide greater stability of the two pieces when connected.

Arm 75 extends rearwardly from the posterior edge of sheath insert portion 74. Arm 75 may be utilized as an attachment point for a soldered lock-wire between arm 75 and sheath 80.

It will be appreciated by those familiar with the art that the vertical sheath and sheath insert are more resistant to being decoupled from one another while in the patient's mouth. The tongue is generally less capable of applying the necessary direct upward or downward pressure which would separate the sheath insert from the sheath. Therefore, arm 75 may be removed where patient comfort is a consideration.

In FIG. 6 the vertical sheath 80 and sheath insert portion 74 of FIG. 5 are shown in their coupled position. Each of insert posts 76 have been placed into sleeves 84 and sheath insert portion 74 pressed vertically to permit indents 78 on each of posts 76 to engage with indents 88 of sleeves 84.

Referring now to FIG. 7 and FIG. 8 the attachment and orientation of sheath 80 (FIG. 5) is shown. In FIG. 7 sheath 80 is shown attached to band 90 which encircles tooth 92. Band 90 is a standard stainless steel band which has been long used in the art. Sheath 80 is attached to band 90 by spot welds on flanges 82. The orientation of indent 88 may be observed and it should be noted that the apex of the triangle is oriented upwardly. FIG. 8 provides a plan view of FIG. 7. The encirclement of tooth 92 by band 90 is shown as well as the orientation of sheath 80 thereon. Also shown is the interior of sleeve 84 of sheath 80 and the inward projection of indents 88 for registration with indents 78 on posts 76 of vertical sheath insert 70 may be observed.

In FIG. 9 and FIG. 10 is shown a typical crimp tube connector which is used to hold a Ni—Ti arch in contact with a sheath insert. As shown in FIG. 9 an arch wire 120 spans the distance between crimp tube connectors 122. Arch wire 120 is inserted into crimp tubes 122 and an insert wire 128 is inserted into the opposite opening of crimp connector 122. When arch wire 120 and insert wire 128 are in place, crimp connector 122 is squeezed to maintain arch wire 120 and insert wire 128 in place within crimp connector 122. This arch appliance 119 is then inserted into a sheath attached to a patient's teeth. This is accomplished by using insert wire 128 to act as a sheath insert. To this end, insert wire 128 is bent back upon itself to provide sufficient size for a friction fit within the sheath.

Referring now to FIG. 10 the double back insert portion 124 which is constructed from insert wire 128 is shown. Incorporated within insert wire 128 is adjusting loop 126 which permits the clinician to lengthen or shorten the distance between arch wire 120 and the sheath in contact with double back insert portion 124. In this manner the arch appliance 119 is modified to the individual patient as well as modified during treatment. It will be appreciated by those skilled in the art that the crimp tube arrangement shown in FIGS. 9 and 10 does not permit multiple arch wires 120 to be incorporated into an orthodontic appliance without joining together multiple crimp tubes. This connecting of crimp tubes by either soldering or welding incorporates one or more points for potential weakness in the device. These weld points can result in breaking apart of the crimp tubes while the device is in the mouth or lead to misalignment of the crimp tube connectors which will affect the efficaciousness of the orthodontic arch appliance. In addition, the double back insert portion 124 of the crimp connector type of insert does not provide any sure lock mechanism with the sheath and is easily worked loose from the sheath by manipulations of the patient's tongue. Further, adjusting loop 126 if improperly positioned may result in misdirection of the forces which are to be applied to the teeth. This can result in ineffective treatment of the patient's orthodontic problem.

In contrast the sheath and sheath insert of the present invention overcomes these limitations of crimp connector type methods of joining Ni—Ti arch wires to a sheath. As previously indicated the arch wires are securely crimped within the sheath insert 30 (FIG. 2) 72 (FIG. 5) in an orientation which may be definitively determined by the clinician prior to insertion of the device within the patient's mouth. In addition, the elimination of adjusting loop 126 eliminates the potential for misalignment of the arch wire with respect to the sheath and sheath insert. Finally, the methods for locking the sheath insert within the sheath avoid the unintentional dislocation of the orthodontic appliance by patient manipulation of the device with the tongue or objects inserted into the mouth.

Figure 11:
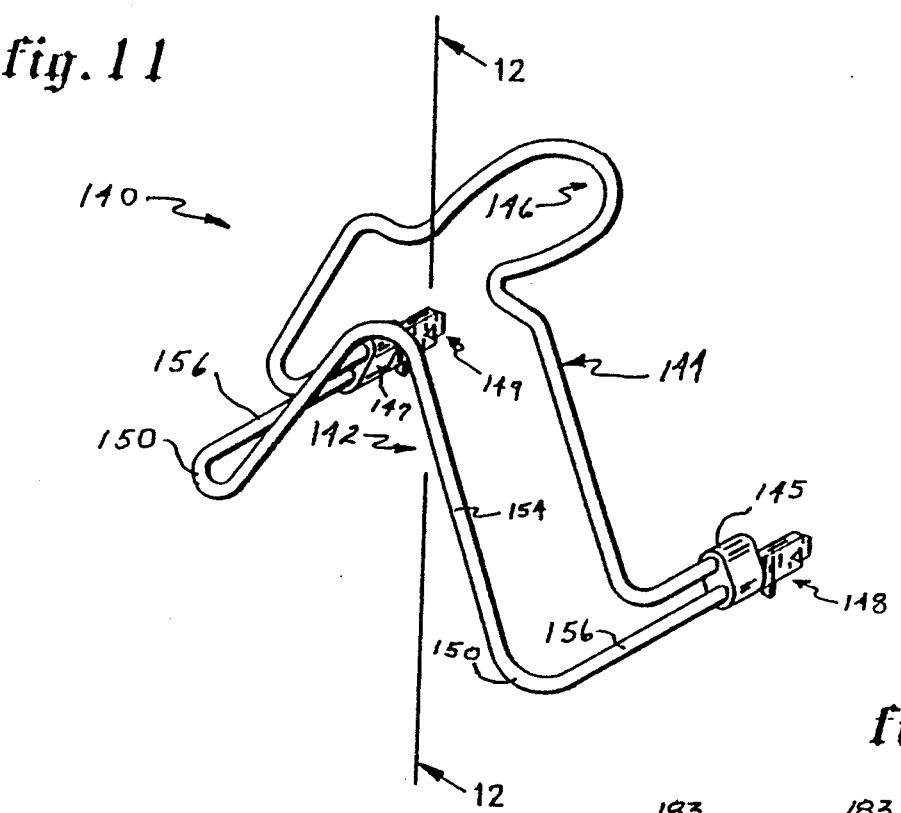
FIG. 11 is a perspective view of the Ni—Ti tandem wire palatal expansion device.
Figure 12:
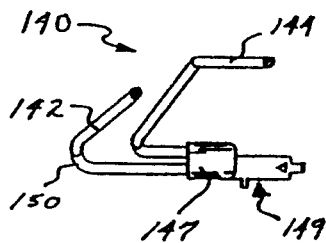
FIG. 12 is a cross-sectional view of the tandem wire device taken along line 12—12 of FIG. 11 and showing the orientation of the arch wires within the sheath insert.

Referring now to FIG. 11, an inventive Ni—Ti tandem wire palatal expansion arch 140 is shown in perspective view. Arch 140 is comprised of lower arch wire 142 and upper arch wire 144. Arch wires 142, 144 are inserted into sheath insert 148, 149 and secured in place by the bilateral crimping of appliance reception portion 33. Arch wires 142, 144 of expansion arch 140 are composed of a near-stoichiometric alloy of nickel and titanium having memory-retaining characteristics. Arch wires 142, 144 extend bilaterally along the palatal concavity to unite sheath inserts 148 and 149. It will be appreciated from the foregoing description that the particular characteristics of sheath insert 148, 149 permit this inventive tandem coupling of arch wires made from nickel-titanium to thereby allow construction of the tandem wire device.

Nickel-titanium tandem arch 140, due both to its tandem wire construction and utilization of a memory-retaining alloy such as nickel-titanium, provides a number of benefits for both the patient and the clinician involved in palatal expansion treatment beyond conventional stainless steel devices. The tandem Ni—Ti wire arch provides simultaneous bilateral expansion of the mandibular cuspids, first bicuspids and second bicuspids.

It has also been observed that a concomitant, spontaneous realignment of the mandibular teeth occurs in response to the increase in width of the maxillary arch by the nickel-titanium tandem arch device. It is believed that this effect is heretofore unobserved in the use of such palatal expansion devices.

Figure 13:
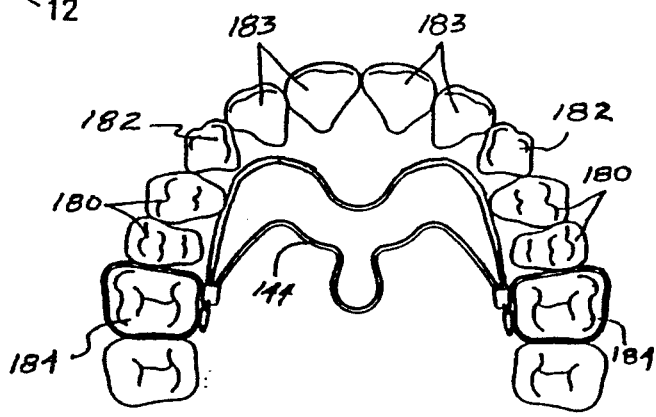
FIG. 13 is a plan view of the upper jaw illustrating the horizontal sheath insert embodiment joining the tandem wire device together and connecting the tandem wire device to a horizontal sheath.

As shown in FIG. 13 bend 150 of lower arch wire 142 abuts against cuspids 182 while arm 156 of lower arch wire 142 abuts against bicuspids 180 (FIG. 13). In this manner as outward pressure is produced by lower arch wire 142 the cuspids 182 and bicuspids 180 are pressed outwardly and thus the anterior portion of the palate is spread to provide additional room for anterior teeth 184 (FIG. 13). This outward force of arm 156 and bend 150 is provided by the general "M-shaped" form of lower arch wire 142.

The operation of an "M-shaped" single arch wire has been described in patent application Ser. No. 07/662,204 having a filing date of Feb. 27, 1991. This application is incorporated herein by reference.

To further enhance the palatal arch expansion characteristics of lower arch wire 142 as discussed both herein and in the above-referenced application, it has become efficacious to incorporate a second Ni—Ti palatal expansion arch wire to function in conjunction with lower arch wire 142. Such an arch wire is presented in upper arch wire 144 (FIG. 11) which generally serves to provide additional force for general expansion of the palate and more particularly to provide additional force directed to the expansion of first molars 184 (FIG. 13).

Referring again to FIG. 11, upper arch wire 144 is shown in position within sheath insert 148, 149. Upper arch wire 144 is mounted above lower arch wire 142 within cavity 50A (FIG. 3). This positioning of upper arch wire 144 is such that contact with bicuspids and 180 and cuspids 182 is avoided and the expansive force provided by upper arch wire 145 is specifically directed into sheath insert 148, 149 which is in contact with first permanent molar 184. This division of the forces which are applied to the various teeth in attempting to expand the palatal arch permits allocation of different magnitudes of force to the various teeth to be operated upon. As previously discussed lower arch wire 142 contacts cuspids 182 and bicuspids 180 directly as well as first permanent molar 184 through its attachment to sheath insert 148, 149. This arrangement of lower arch wire 142 permits force to be applied to each of these teeth. The arrangement of upper arch wire 144 within tandem wire arch appliance 140 permits the application of additional pressure directly to the first permanent molar. Therefore, this unique arrangement of Ni—Ti tandem wires within palatal arch expansion appliance 140 permits the use of smaller wire dimensions for each of lower arch wire 142 and upper arch wire 144 thereby generating lower force values at any particular point.

This provides greater patient comfort while at the same time permitting more specific control over the application of expansive forces to the palate. In addition, the use of multiple wires for the application of force to the teeth and palate allows the clinician to select wires of different dimensions, and therefore, different degrees of force generation, in the various positions of the tandem wire expansion arch.

This ability of the clinician to utilize wires of different dimension and different force generation permits allocation of forces to the teeth in a more efficient manner for tooth movement. For example, where it is observed that the cuspids 182 and bicuspids 180 are not substantially out of proper-position the clinician may select a wire of smaller diameter and therefore lesser force generative capacity to abut these teeth. Further, the clinician, observing that first permanent molars 184 are substantially rotated or deflected inwardly and being aware of the greater mass of first permanent molar 184, may choose a wire of greater diameter to impart additional correctional forces to first permanent molar 184.

The Ni—Ti tandem wire palatal expansion arch appliance 140 offers a number of features and benefits heretofore unavailable in stainless steel type expansion arch devices. The first of these benefits is immediately apparent upon attempting to apply the inventive device within the mouth of a patient. It will be appreciated by those skilled in the art that a lingual sheath, such as that shown in FIG. 1, when attached to a tooth will not be presented at a convenient angle for insertion of the expansion arch device.

Figure 14:
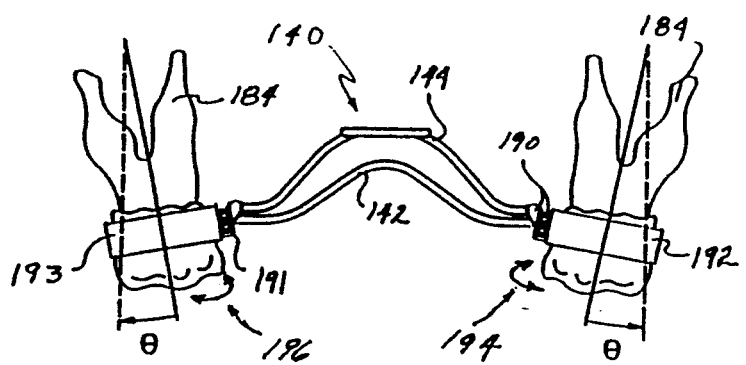
FIG. 14 is a side elevational view of two opposing upper molars which are inwardly biased and showing horizontal sheaths attached thereto with the Ni—Ti tandem wire device connected thereto by the horizontal sheath insert.

As shown in FIG. 14 it can be expected that a sheath 190 attached to band 192 on molar 184 will necessarily be in a skewed position due to the irregular position of molar 184. In FIG. 14, molars 184 are shown inwardly displaced or canted from vertical by angle theta. The degree of displacement illustrated by angle theta will also be present in the horizontal orientation of sheath 190. In addition, this inward deviation of molars 184 presents sheath 190, 191 in closer proximity to one another than are sheath inserts 148, 149. It will also be appreciated that molars 148, 149, having bands 192, 193 attached and sheath 190, 191 attached thereto respectively, may present a rotational deviation of the molar as indicated by rotational movement arrows 194, 196. Movement of molar 184 in either direction indicated by rotational arrows 194, 196 will present a third degree of misalignment of sheath 190, 191 with respect to the orthodontic appliance for insertion into sheath 190, 191. The end result of this misdirection of sheath 190, 191 is that insertion of the orthodontic appliance 140 into the sheath is inhibited and requires some amount of compression or misshaping of the orthodontic appliance.

In stainless steel type devices, the amount of freedom available to the clinician to compress or twist or otherwise bend the stainless steel type device to allow insertion into the sheath is limited. Therefore, the clinician must incorporate stress relief points in the stainless steel device by bending the device in such a manner as to allow the insertion of the appliance into sheath 190, 191. This results in multiple return visits of the patient to the clinician for removal of the stress relieving bends as the teeth slowly conform to the pressures applied by the device. This presents a great deal of the time and expense involved in such corrective procedures.

By contrast the nickel-titanium tandem wire palatal expansion arch appliance avoids these difficulties of the prior art devices by being substantially compressive and elastic thereby permitting the clinician far greater latitude in the degree to which the device may be misshapen for placement within the mouth. The compressing or twisting of the nickel-titanium tandem wire device, wire permitting insertion of the device into sheath 190, 191 does not result in deformation of the appliance as lower arch wire 142 and upper arch wire 144 do not structurally yield by the manipulations of the clinician in inserting the device.

Rather, as the device is in its "martensitic" state the nickel-titanium alloy is comparatively soft and may be deformed and twisted with relative ease and without causing permanent conformation changes in the appliance. As the nickel-titanium arch wires 142, 144 begin to warm to body temperature in the mouth the nickel-titanium alloy begins to change its physical state. The Ni—Ti begins the transition from its "martensitic" state where it is flexible into its "austenitic" state within which the metal seeks to return to a predetermined shape. This predetermined shape has been provided to the device in its original manufacture by heating the nickel-titanium alloy arch wire 142, 144 segments of the apparatus at 1200° F. while under a six percent strain. This high temperature treatment of the Ni—Ti alloy provides it with its "memory" shape to which it seeks to return when it is in its austenitic state.

It is this ability of the nickel-titanium alloy utilized in the present invention which enables results which are unexpected with respect to similar devices constructed of prior art materials. As it may now be appreciated by the foregoing description that the inventive orthodontic appliance may be substantially misshaping during insertion, it will also be appreciated that the "misshaping" of the device to allow insertion into the sheaths results in forces being applied to the teeth which are a direct result of the misshaping of the tandem arch device as it is inserted into the sheaths. That is, as the inventive device 140 warms within the mouth and attempts to return to its "memory shape" it will begin to apply forces to the teeth which are in direct response to the direction and amount of misshaping the expansion arch appliance 140 has incurred during the insertion process.

Thus it can be appreciated that the device applies a "dynamic" type of force to the teeth providing varying degrees of outward force as well as rotational and torque forces to the teeth and that these forces will vary throughout the movement of the device back to its "memory shape". As the "memory shape" represents the proper position of the teeth, once the teeth have been realigned into the correct position the nickel-titanium tandem arch device will have achieved its memory position and will cease the application of force to the teeth.

In the case of prior art stainless steel type of devices providing only a one directional spring-type pressure to the misaligned teeth, the patient would require repeated office visits so that the clinician could conduct a step-by-step modification of the shape of the stainless steel device to redirect the spring forces of the device to accomplish correction of the teeth positioning.

Figure 15:
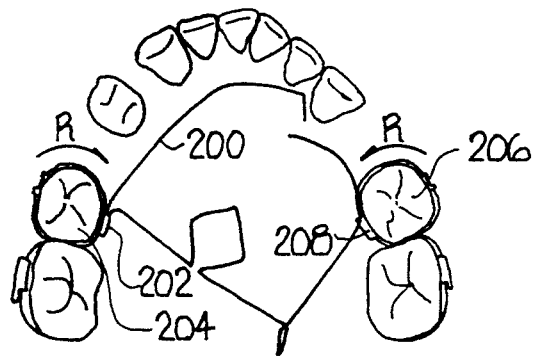
FIG. 15 is a plan or occlusal view of the lower jaw illustrating a prior art stainless steel orthodontic device connected on one side to a sheath attached to a molar.
Figure 16:
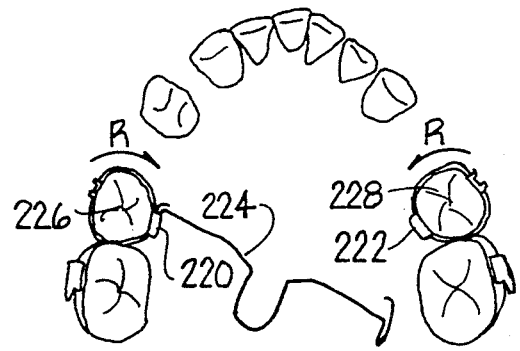
FIG. 16 is a plan or occlusal view of the lower jaw illustrating a prior art stainless steel arch expansion device connected on one side to a sheath attached to a molar.

Referring now to FIGS. 15 and 16 the standard stainless steel type devices of the prior art are illustrated partially inserted into a lingual sheath attached to a molar. In FIG. 15 a stainless steel archwire device 200 is shown partially inserted into a sheath 202 which is attached molar 204. Molar 204 is slightly rotated inwardly as is its counterpart molar 206. This inward rotation "R" is a common orthodontic malalignment in need of correction. However, with the prior art stainless steel devices the attempt to place archwire device 200 into sheath 202, 208 attached to rotated molars 204, 206 results in device 200 being misaligned with respect to the teeth to be acted upon. This necessitates bending of the stainless steel archwire in an attempt to achieve proper orientation of the archwire within the mouth.

In severe eases of molar rotation placement of the device within the sheaths attached to rotated molars 204, 206 may be nearly impossible due to the severe inward rotation in the direction of arrow "R". As stainless steel is inelastic, the orthodontist must bend apparatus 200 in order to successfully insert the device within sheath 202, 208. Once the device is sufficiently misshapen to be installed, the orthodontist must incrementally bend the device back toward its original configuration as movement of rotated molars 204, 206 presents sheath 202, 208 in a corrected position.

This incremental shaping of device 200 results in high corrective forces being imparted to molars 204, 206 immediately after each new modification to device 200 by the orthodontic clinician. These corrective forces, while initially very high, are of short duration. The tooth within one or two days moves that amount of distance provided by the incremental modification of the stainless steel device. The corrective force is then dissipated and further correction of the tooth must await the next incremental modification of the stainless steel device.

This limitation of intermittent application of corrective forces is necessitated by the rigidity of the prior art stainless steel devices. Stainless steel devices are capable only of generating a force over the short distance and in the specific direction provided by the bending of the device. The orthodontic clinician by repetitive bending generates successive incremental corrective forces to adjust the teeth and to re-form shape of the stainless steel device. Each time the readjusted device is applied to the teeth it imparts an initially very high, but short lived force which causes an initial rapid movement of the tooth over a short distance. The application of high force is followed by cessation of movement as soon as the tooth has moved beyond the influence of the force provided by the incremental bend. This type of application of force to the tooth results in repeated painful episodes for the patient as the modification to the device causes rapid movement of the tooth resulting in shearing of the supporting tissues.

Referring now to FIG. 16 a second prior art stainless steel device is presented which is used for rotating the teeth to which it is applied. Again, it may be observed that sheath 220, 222 are inwardly rotated in the direction of arrows "R". Once again, insertion of device 224 into sheath 220, 222 cannot be accomplished without modification of the shape of device 224. The clinician must manipulate stainless steel device 224 by bending the device out of its intended shape in order to apply it to the rotated sheath 220, 222.

Even if molars 226 and 228 are not rotated and are in an ideal position for receiving device 224, the previously described stop-start type of force of stainless steel is still the only type of corrective activity provided. In the situation where the molars are not rotated and the device is properly positioned against the teeth to be acted upon the orthodontic clinician must provide the moment of force by bending the stainless steel appliance to generate the spring-type forces supplied by the stainless steel to bring corrective pressure to bear on the misaligned tooth.

The inventive method and devices for practice of the inventive method contemplated herein avoid the stop-start force applications of stainless steel devices by relying on the application of very low, but constant, expansive and rotational forces. These forces are generated constructing the orthodontic device of a shape memory-retaining alloy, such as a nickel-titanium alloy or beta-titanium alloy or super-elastic nickel titanium alloy or nickel-titanium-copper alloy, which attempts to modify its shape configuration when the alloy is warmed to its austenitic state while within a patient's mouth.

While nickel-titanium alloy has been used in orthodontics to take advantage of the alloy's flexibility, this alloy has not been utilized for palatal expansion or tooth rotational orthodontic applications. Historically, the forces used by orthodontic clinicians for these expansion and rotation adjustments have been quite high. The treatment methods standardly employed provide forces commonly in the range of 6 to 25 lbs. for the technique known as "rapid palatal expansion" and forces of 2 lbs. or more for the orthodontic methodology known as "slow palatal expansion" or "low force palatal expansion". These types of treatments have relied upon stainless steel devices using jack-screws and have occasionally incorporated a stainless steel spring for application of force.

As is the standard case with stainless steel devices, force is initially applied by the device to the misaligned tooth at a very high level. This is followed by sudden movement of the tooth and a rapid fall off in the corrective pressure applied to the tooth. As the initial sudden movement of the tooth is just hours after adjustment of the orthodontic device by the orthodontist treatment of the orthodontic misalignment is ended until the next appointment with the orthodontist. This sudden reduction in force is illustrated in FIG. 33 where the force of the stainless steel appliance can be seen to rapidly fall to near zero within hours of manipulation of the device by the orthodontist.

In the technique known as rapid palatal expansion, devices are applied to the maxillary or mandibular arches which produce initial pressures of 6 to 10 lbs. with the Multiple daily manipulations of the device can result in cumulative loads of 20 lbs. or more. These high pressures disruptively overwhelm the tissues of the maxilla suture as well as providing outward movement of the teeth themselves. These high forces are achieved by implantation of jack-screw across the molars which generates initial high pressures each time the screw is rotated.

The alternative to "rapid palatal expansion" has been the "slow palatal expansion" procedure. This involves use of stainless steel lingual wire appliances equipped with springs to apply forces of approximately 2 lbs. The slow expansion procedures increase the amount of orthodontic movements (tooth movement within the palatal arch) and tend to minimize the orthopedic separation of the maxillary suture which results from the higher pressures of the rapid palatal expansion technique.

In neither of these standard treatments for expansion of the palatal arch and adjustment of malaligned teeth has the attempt been made to use comparatively extremely low forces on a continuous basis in order to achieve expansion and rotation while avoiding the harsh effects of the high forces of rapid palatal expansion as well as the comparatively high force involved even in the slow expansion techniques. Heretofore it has not been considered possible to achieve effective results in these orthodontic activities when forces below 2 lbs. were utilized. In fact, proponents of rapid palatal expansion have for many years asserted that the 2 lb. pressures of the slow expansion technique were insufficient and unnecessarily prolonged the treatment.

In direct contrast to these prior teachings the present inventive method and apparatus relies on the constant low forces which may be generated through use of nickel-titanium alloys and other temperature-affected metals having a shape memory-retention. This new method provides for expanding the pallet and rotating misaligned teeth through the use of a memory metal alloy in its austenitic phase to apply a constant low force to the affected teeth to achieve their slow and gentle repositioning. This method slowly expands the maxillary suture at a rate which promotes the reorganization of tissue about the suture as it expands. The method provides greater stability for regeneration of the palatal suture while avoiding the significant deformation of maxillary bones which follows with rapid palatal expansion. In addition, some researchers believe that with rapid palatal expansion the degree of tissue stress caused actually increases the required retention periods to allow reorganization and stabilization of the maxillary suture and avoid skeletal relapse. This too is avoided.

The inventive continuous low force method of treatment provides far greater patient comfort. The pressures applied to the teeth are from 4 to 20 times less than the conventional recommended forces. Therefore the substantial discomfort that can arise from the high forces associated with rapid palatal expansion and even the lower forces of the slow expansion technique is not present.

The method also provides the patient the ability to control metallurgical state of the device while it is in place in the mouth. The patient can shift the device from its more rigid austenitic state or phase into its more relaxed martensitic state by cooling the device to a temperature below its transition temperature with a drink of cold water. This allows greater comfort for the patient and provides increased adherence to treatment plans.

A particular problem which arises with the prior art methods of expanding the palate is that frequent visits to the orthodontic clinician are required to adjust the device. In the case of jack-screw devices, patient participation is required to advance the jack screw on a daily basis. This can result in daily discomfort to the patient and patient involvement in the treatment which can be extremely variable and dependent upon the patient's willingness to comply with therapy.

Figure 17:
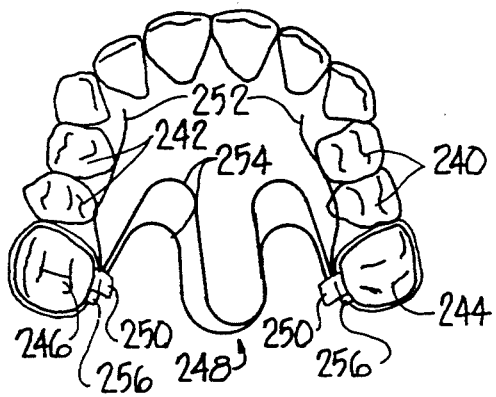
FIG. 17 is a plan or occlusal view of the upper jaw illustrating a twin memory metal arch expansion device with stainless steel extenders in a partially compressed state for insertion into an unexpanded upper jaw.
Figure 18:
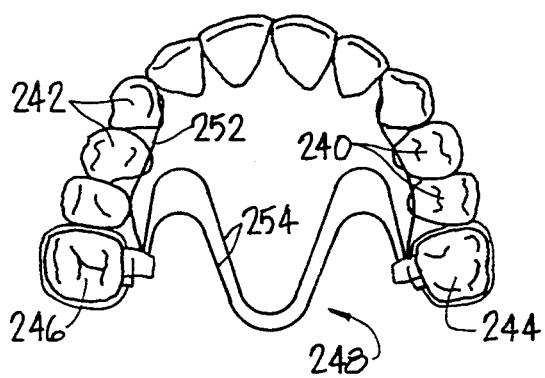
FIG. 18 is a plan or occlusal view of the upper jaw of FIG. 17 after expansion of the upper jaw arch by the inventive device and showing rotation of the molars and outward expansion of the premolars.

Referring now to FIGS. 17 and 18 one embodiment of a device employed in application of the inventive method is illustrated. In FIG. 17 an occlusal view of the upper or maxillary arch is shown with premolars 240, 242 compressed inwardly and molars 244, 246 slightly rotated. The nickel-titanium alloy device 248 is shown attached to sheath insert 250 with stainless steel extenders 252 in contact with premolars 240, 242. The M-shaped wires 254 of device 248 are composed of a shape memory-retaining type metal alloy such as nickel-titanium. The device is applied with the alloy in its martensitic state which permits manipulation and compression of the device to allow it to be fitted into sheath 256.

As the nickel-titanium alloy has its transition temperature (approximately 94° in the particular alloy of this embodiment) below mouth temperature it is in its martensitic state and may be manipulated to the specific configuration of the patient's misaligned palatal arch and the sheath positions resulting therefrom to permit installation of the device without bending it as with stainless steel devices. Once the device is inserted in the mouth, it warms to its austenitic state whereupon it becomes more rigid and attempts to restore itself to the specific configuration instilled in it during its formation by heating at 1,200° F. while under a 6 percent strain.

The device will therefore exert a constant, but very low force against the misaligned teeth as it attempts to regain its austenitic state conformation. In this manner the device continues to operate on the misaligned teeth during each moment of its installation until it eventually arrives at its original conformation as represented in FIG. 18. In FIG. 18 the device can be seen to have expanded the palatal arch to a desirable dimension and has succeeded in rotating molars 244, 246 into proper orientation. In FIG. 18 the device has achieved its austenitic state conformation and can remain in place for a period of weeks to provide retention of the teeth in a proper alignment while the bony material of the jaw surrounding the teeth forms to securely hold the teeth in their newly oriented position. As archwires 254 expanded to their austenitic conformation and then ceased to exert pressure on molars 244, 246 stainless steel extenders 252 provided an associated outward pressure on premolars 240, 242 so that they were moved outwardly with the advancing molars 244, 246. In this fashion the entire maxillary arch has been expanded in a fashion not before contemplated by the prior art and while posing little discomfort to the patient and without requiring any patient participation.

Figure 19:
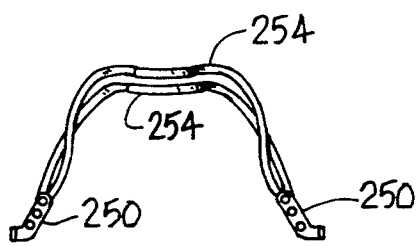
FIG. 19 is a rear elevational view of the device of FIGS. 17 and 18 showing the attachment of the memory metal arch wires within the sheath insert and showing the receptacle for the extenders.

In FIG. 19 the device of FIGS. 17 and 18 is shown from the rear and in elevational view. Archwires 254 may be seen as they are mounted in sheath insert 250. Stainless steel extenders 252 are hidden from view. In FIG. 19 the inventive sheath insert 250 is shown which is specifically developed for the capture and holding of shape memory-retaining type metals which cannot be soldered into conventional devices.

Figure 20:
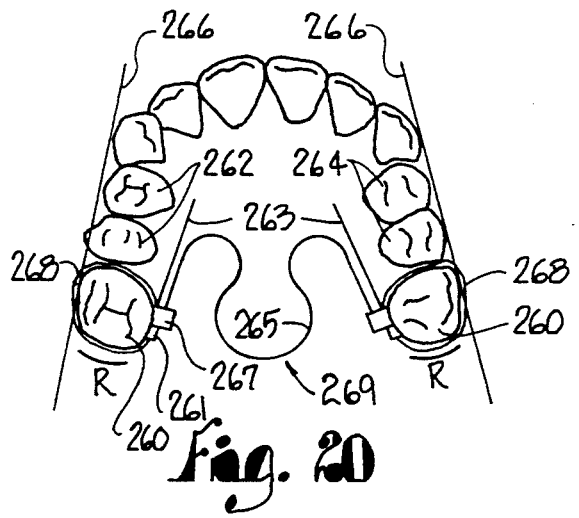
FIG. 20 is a plan or occlusal view of the upper jaw before expansion by the memory metal single loop rotator and distalizer apparatus shown with a stainless steel stabilizer extending from the sheath insert.
Figure 21:
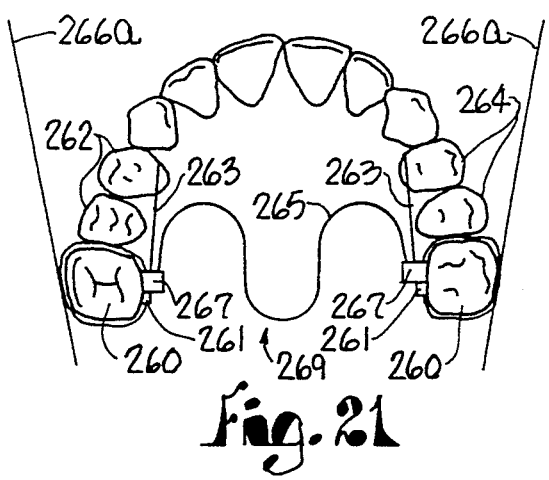
FIG. 21 is a plan or occlusal view of the upper jaw of FIG. 20 after expansion by the memory metal rotator and distalizer device which is shown in its position after expansion of the arch has occurred.

Referring now to FIGS. 20 and 21 a maxillary Ni—Ti single loop rotator and distillizer with stabilizers is shown in position. In FIG. 20 a maxillary dental arch before rotation of the molars and distilization is shown. In this device the molars 260 are rotated in the direction of arrows "R" and premolars 262, 264 are collapsed inwardly. To properly align these teeth it is necessary not only to rotate molars 260, but to push them rearwardly or distally in order to gain additional space in the maxillary dental arch for proper positioning of premolars 262, 264. The improper positioning of these teeth is illustrated by directional lines 266 which show the orientation of the buccal portion of molars 260.

Referring now to FIG. 21 the maxillary arch of FIG. 20 is shown after expansion and rotation of the teeth. Molars 260 have been rotated so as to align the buccal surface in proper conformation as shown by directional lines 266a. Stabilizers 263 have progressed outwardly with the rotation and expansion caused by device 261 as nickel-titanium archwire 265 moved into its austenitic state conformation. This rotation and outward movement served to press premolars 262, 264 into an outwardly expanded position. As the operation of the device of FIGS. 20 and 21 indicates more than a single direction of movement can be accomplished through the use of the method of expansion and rotation of the inventive memory metal devices. In the treatment situation examined in FIGS. 20 and 21, the device accomplished the lateral expansion of the maxillary arch, the rotational movement of the molars and the rearward or distal movement of the molars without any manipulation of the device after its installation. This results from the shape memory-retaining metal alloys utilized in the method to seek their austenitic state conformation when warmed in the mouth. This causes movement of the device in all three directional planes and corresponding corrective force to the teeth.

By contrast, in the stainless steel device, the orthodontic clinician would be required to provide multiple directional bends to create moments of force in the desired direction of action. As the range of motion and amount of force of stainless steel is strictly limited, the patient would be required to make multiple visits to the orthodontic clinician to have the stainless steel archwire manipulated in order to first rotate molars 260 and then press them outward as well as rearwardly to increase room for premolars 262, 264. In the devices of the inventive method far more is accomplished. A device utilized in the inventive method may have a shape similar to prior art stainless steel devices and yet be capable of accomplishing far more than the equivalent stainless steel device.

To apply the device of FIG. 20 to the patient, the archwire with stabilizers is first cooled to fully develop its martensitic state so the device may be compressed and manipulated to fit sheath insert 267 within the sheath 261 attached to bands 268 on molars 260. Once in place, the device warms to its austenitic state and attempts to revert to its austenitic state conformation. This results in the device both pulling and pushing on the misaligned teeth—a feature not heretofore available in stainless steel orthodontic archwires. It will be appreciated by those skilled in the art that the forces provided by the devices utilized in the inventive method apply forces in response to the degree and direction which the device is misshapen from its austenitic conformation. Therefore, the direction and continuation of force to which the misaligned teeth are subjected is directly a function of their deviation from the austenitic conformation of the device. If the archwire is originally formed to the proper final dimensions for the teeth or dental arch, the misaligned teeth will, by virtue of their degree of distortion from the final austenitic configuration of the device determine the direction and amount of force which is applied to them. In this manner the method and device can operate largely independent of additional manipulations by an orthodontic clinician.

Figure 22:
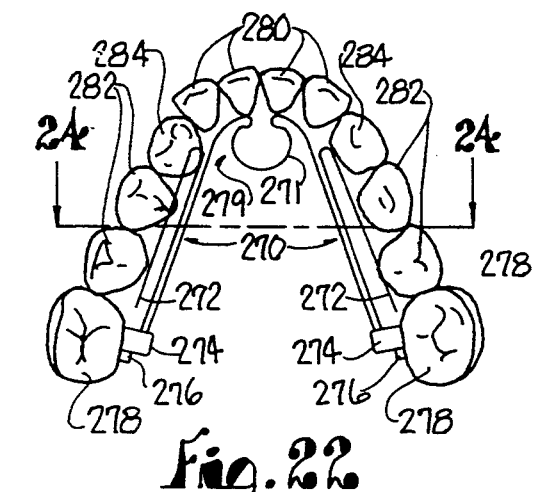
FIG. 22 is a plan view of the lower jaw prior to expansion showing a single loop transverse expander device with adjacent stainless steel spring in compressed position.
Figure 23:
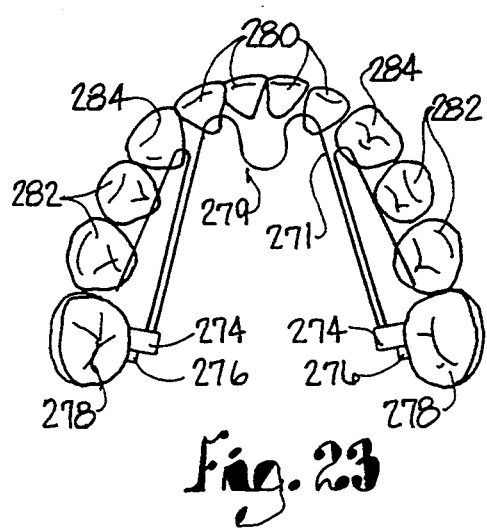
FIG. 23 is a plan or occlusal view of the lower jaw of FIG. 22 after expansion by the device of FIG. 22 and showing the device in its relaxed expanded position.

Referring now to FIGS. 22 and 23 the operation of a mandibular single loop nickel-titanium transverse arch expander having adjacent stainless steel springs will be described. The device of FIG. 22 is designed to operate under the inventive method to expand the anterior portion of the mandibular arch and to allow application of clinician-selectable outward forces by the manipulation of stainless steel springs 272. The mandibular expander device 270 is composed of a shape-memory alloy metal archwire 271 which is mounted in sheath inserts 274 connected to sheath 276 attached to bands on molars 278. The anterior portion of device 270 has a loop area 279 which may be compressed while in its martensitic state to conform to the collapsed position of incisors 280. Upon device 270 being warmed within the mouth to its austenitic state, the device begins to change into its austenitic conformation from the shape into which it was manipulated while in its martensitic state. This causes application of a very low, but continuous outward pressure to incisors 280. While this mechanical counter-force is being applied to the teeth the clinician can utilize stainless steel springs 272 to accomplish outward movement of the premolars 282 and bicuspids 284. The specific manner of manipulation of stainless steel springs 272 will be discussed infra.

Figure 24:
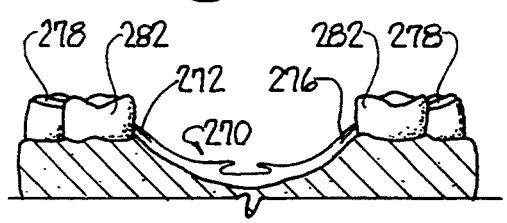
FIG. 24 is a cross-sectional view of the device of FIGS. 22 and 23 taken along line 24—24 of FIG. 22 showing the confirmation of the device to the concavity of the mouth.

Referring to FIG. 23, the expanded position of the mandibular arch of FIG. 22 is shown. Incisors 280 have been expanded by loop 279 which has now moved into its austenitic state conformation. Stainless steel springs 272 have acted against premolars 282 and bicuspids 284 to push these teeth outwardly to overall expand the mandibular arch. Referring to FIG. 24 the device of FIGS. 22 and 23 is shown in cross-sectional view indicating the position of the device in relation to the soft tissue of the jaw to avoid interference with the tongue just above.

Figure 32A:
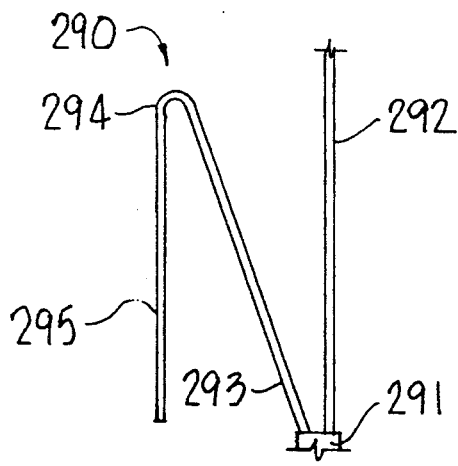
FIG. 32A illustrates in fragmentary plan view one possible configuration of a spring extender, in this case being cantilevered outwardly from the point of connection with the sheath insert, the spring extender has also been bent outwardly from the forward loop to provide additional pressure proximate to the teeth near the sheath insert.
Figure 32B:
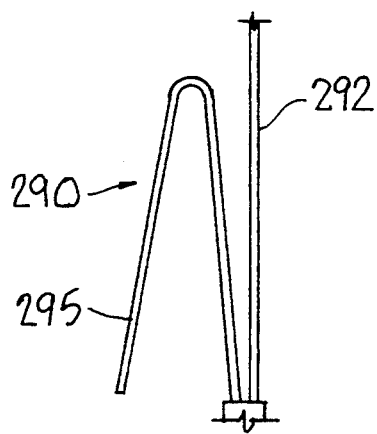
FIG. 32B shows a spring extender similar to that of FIG. 32A, with the extender been bent outwardly from the forward loop in order to provide additional outward movement of the teeth proximate to the sheath insert.
Figure 32C:
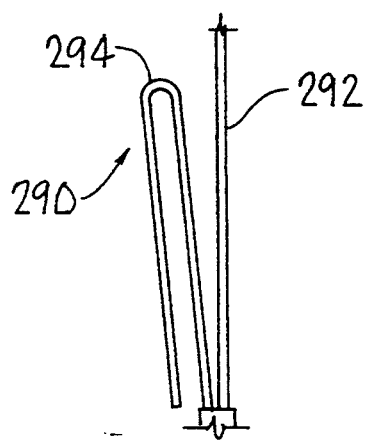
FIG. 32C illustrates a spring extender being bent outwardly only slightly from the point of insertion into the sheath insert to provide additional pressure on anterior teeth.
Figure 32D:
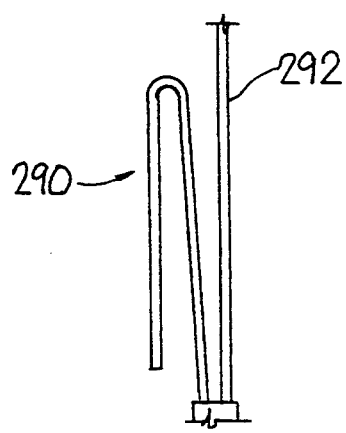
FIG. 32D illustrates a spring extender being in a generally inactivated position and serving as a stabilizer for the orthodontic device to which it is attached.

Referring now to FIGS. 32A-32D the action forces applied to the teeth by stainless steel springs 272 of FIGS. 22, 23, 25, 26 will be described. In FIG. 32A a spring 290 is shown positioned in sheath insert 291 and adjacent to archwire 292. This orientation of the spring provides the orthodontic clinician with a number of options which may be utilized to apply pressure of various amounts and directions to the premolars and bicuspids. In the orientation of FIG. 32A the spring has been bent outwardly at area 293 which is adjacent to its anchorage in sheath insert 291. This bend may be used to provide force against the bicuspid which would be adjacent to curve 294 of the spring device. Free arm 295 of spring 290 also may be adjusted to provide various degrees of pressure on the adjacent premolars. In FIGS. 32B-D variations on these manipulations of the spring are shown. In FIG. 32B free arm 295 has been moved outwardly to provide additional pressure on the premolars. In FIG. 32C the curve portion 294 has been moved to specifically impact the bicuspid. In FIG. 32D the spring has been only slightly adjusted outwardly to provide a mild force against both the premolars and the bicuspid.

Figure 30:
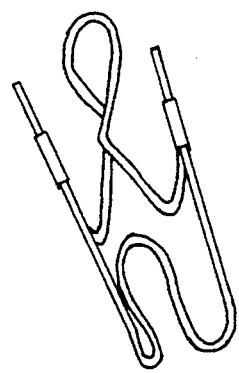
FIG. 30 illustrates one configuration of the inventive devices in their martensitic state allowing the device to be twisted and compressed and manipulated for insertion into the mouth of a subject.
Figure 31:
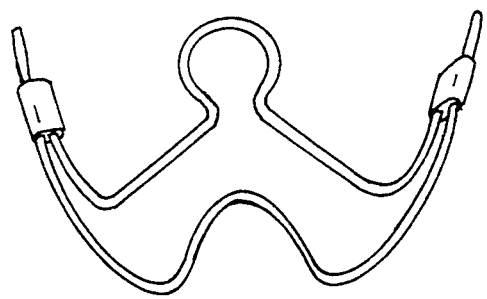
FIG. 31 illustrates the device of FIG. 30 after it has been warmed to its austenitic state causing it to revert to its original configuration.

Referring now to FIGS. 30 and 31 the manipulation of the shape memory-retaining metal archwires in the various states may be seen. In FIG. 30 a nickel-titanium or memory metal archwire has been cooled to its martensitic state. This allows the device to be compressed and manipulated for insertion into the sheaths attached to bands around misaligned teeth. Once the device has been inserted into the mouth it then begins to warm to its austenitic state or phase. In the austenitic state the metal seeks to reorient itself into the conformation originally provided to it as it was formed.

Thus, in FIG. 31 is shown the device of FIG. 30 once it has been warmed into its austenitic state and spontaneously configures itself into the austenitic state conformation. It will be appreciated that once the archwire has achieved its austenitic configuration it is no longer actively providing forces against the teeth to which it is attached or abuts. Rather, it is at that point serving only to retain the teeth in the confirmation presented. This will allow teeth that have achieved their proper configuration as a result of the device to be retained in that position until the adjacent bone structure is sufficiently developed to hold the teeth in their new position.

Figure 25:
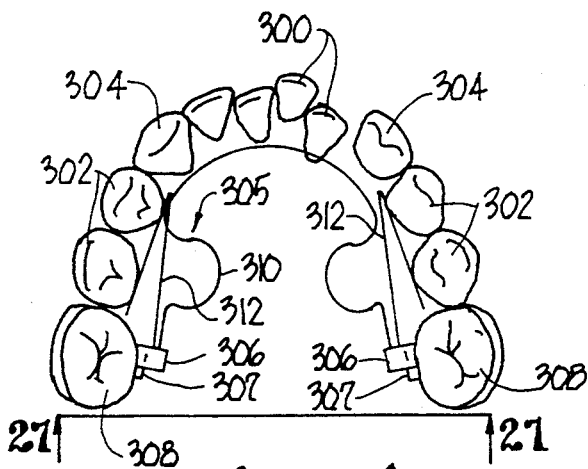
FIG. 25 is a plan or occlusal view of the lower jaw illustrating misaligned anterior teeth and compressed posterior teeth with a tandem loop anterior-posterior expander with adjacent spring extenders positioned prior to expansion.
Figure 26:
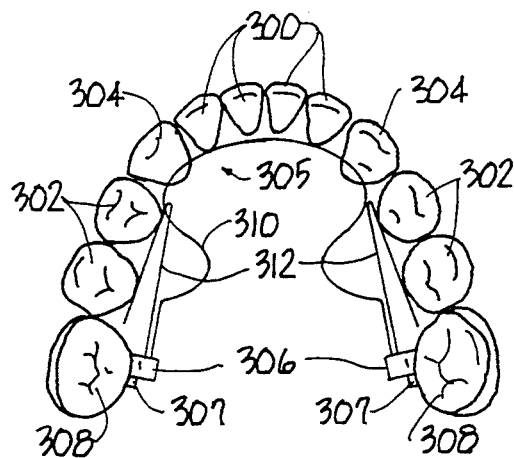
FIG. 26 is a plan or occlusal view of the lower jaw of FIG. 25 after expansion has taken place to expand and reposition the anterior teeth and expand the arch.

Referring now to FIGS. 25 and 26 the operation of a nickel-titanium mandibular tandem loop anterior-posterior expander with adjacent spring extenders will be examined. In FIG. 25 an occlusal view of a mandibular arch is presented showing misaligned teeth with several incisors 300 intruding into the center of the mandibular dental arch. The position of premolars 302 and bicuspids 304 is substantially correct. The tandem loop device 305 is connected to sheath inserts 306 which are attached to sheaths 307 about molars 308. The nickel-titanium or other shape memory-retaining metal archwire extends anteriorly to approach incisors 300. However, archwire 310 is limited by the encroaching incisors 300 and therefore is slightly compressed.

Upon activation of the device, it warms and is transformed into its austenitic state and a constant low pressure is provided against incisors 300 which are slowly moved forward and into their desired position shown in FIG. 26. At the same time, stainless steel springs 312 may be utilized to either stabilize or press outwardly on premolars 302 until their desired expansion is achieved.

Figure 27:
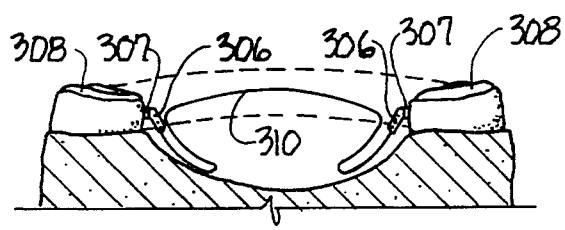
FIG. 27 is a cross-sectional view taken along line 27—27 of FIG. 25 showing the position of the device of FIGS. 25 and 26 with respect to the concavity of the lower jaw.

Referring now to FIG. 27 the device of FIGS. 25 and 26 is shown in cross-sectional view taken along line 27—27 of FIG. 25. In FIG. 27 the downward angle of the archwire 310 toward the jaw may be observed. This configuration allows the device to avoid abrading the base of the tongue.

Figure 28:
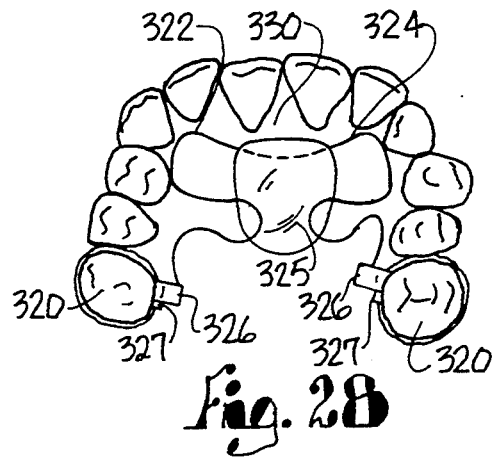
FIG. 28 is a plan or occlusal view of the upper jaw illustrating the application of the shape memory metal maxillary molar distalizer with palatal anchorage in place in a misaligned and compressed jaw.
Figure 29:
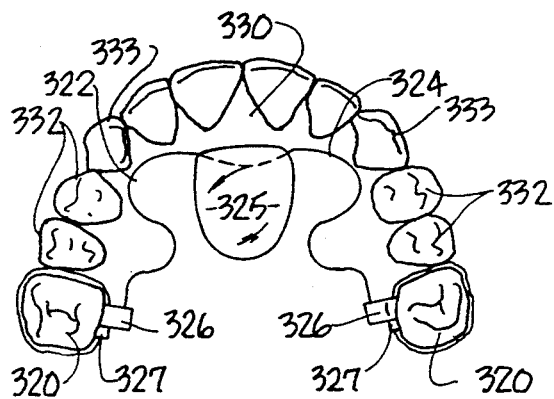
FIG. 29 is a plan or occlusal view of the upper jaw of FIG. 28 after action of the distalizer device of FIG. 28 in moving the molars to provide expansion of the arch.

In FIGS. 28 and 29 the operation of a tandem loop nickel-titanium maxillary molar distillizer with palatal anchorage is illustrated. This device is utilized to apply the inventive method to shift molars 320 rearward or distally from their position illustrated in FIG. 28 and in this matter provide additional space to the maxillary arch allowing the other teeth to shift into expanded positions. This is accomplished by anchoring nickel-titanium loops 322, 324 into vinyl cushion 325. The other ends of archwires 322, 324 are fixed in sheath inserts 326 attached to sheaths 327. During use, vinyl cushion 325 presses against the inclined walls of the palatal vault and lingual alveolar plate 330. In this manner the front of the device is anchored in the anterior portion of the maxillary arch allowing the forces to be directed rearwardly to distilize molars 320. In FIG. 29 distilized molars 320 are shown which have allowed premolars 332 and bicuspids 333 to also move into a correct orientation.

In the fashion illustrated by the previous devices the application of the inventive method, and the devices used therein, may be appreciated as a novel and less rigorous method for expansion of a patient's maxillary or mandibular arch and for accomplishing rotation and distilization of misaligned teeth.

It is important to note that the nickel-titanium tandem arch device provides the type of pressure to the palatal arch which is believed ideal, but has heretofore been lacking in prior art devices. This pressure is a constant pressure which is of a soft and uniform nature which results in expansion of the teeth and palatal arch generally while allowing incremental separation of the palatal suture thereby permitting proper bone plating. The inventive tandem arch device provides pressures in the range of 150 to 200 grams initially. This application of low force is accompanied by a uniform linear force decay over time as the palatal arch is expanded. Such uniform decay of low pressure forces is considered more desirable for physiologic bone response.

It is to be understood that while a certain form of the invention has been illustrated nad described, it is not limited thereto, except insofar as such limitations are included in the following claims and the allowable functional equivalents thereof.

What is claimed and desired to be secured by Letters Patent is as follows:

1. An orthodontic appliance for expansion of the maxillary or mandibular arch comprising:
   a pair of bilaterally extending arch wires composed of a near-stoichiometric alloy of nickel and titanium having memory-retaining shape characteristics,
   a first of said pair of bilaterally extending arch wires having a concave shape and terminating in a pair of ends, said ends being secured within means for connecting said ends to laterally spaced teeth, and
   a second of said pair of bilaterally extending arch wires positioned generally behind said first arch wire, and having a concave shape and terminating in a pair of ends, said ends being secured within means for connecting said ends to laterally spaced teeth such that as said appliance changes to its austenitic state a substantially constant low force is applied by said arch wires to said teeth.

2. The appliance as claimed in claim 1, wherein the inverse martensitic transformation of the nickel-titanium alloy terminates at a temperature below normal body temperature.

3. The appliance as claimed in claim 1, wherein the diameter of said arch wires is at least 0.030 inch.

4. The appliance as claimed in claim 1, wherein the composition of the nickel-titanium is at least 50.5 atomic percent nickel.

5. The appliance as claimed in claim 1, wherein the composition of the nickel-titanium alloy is at least 50.5 and not more than 51.0 atomic percent nickel with the remainder being titanium.

6. The appliance as claimed in claim 1, wherein at least one of said arch wires further comprises an anteriorly extending loop segment.

7. The appliance as claimed in claim 1, wherein at least one of said arch wires further comprises a posteriorly extending loop segment.

8. The orthodontic appliance as claimed in claim 1, wherein said applied force is less than approximately 1.6 pounds.

9. The orthodontic appliance as claimed in claim 1, wherein said applied force is less than 450 grams.

10. A method of expanding the mandibular or maxillary dental arch and correcting molar malalignment comprising the steps of:
forming an archwire composed of a temperature-affected material having a transition temperature below normal mouth temperature into a configuration that is larger than the unexpanded shape of the selected dental arch when said archwire is in an austenitic state,
attaching said archwire to lingually projecting sheaths of opposed molars,
allowing said archwire to achieve an austenitic state, and
exerting with said archwire a continuous low-pressure corrective force against said molars to expand the dental arch and adjust the rotation, and malalignment of said molars.

11. The method as claimed in claim 10 wherein said temperature-affected material is an alloy comprised of nickel and titanium in sufficient proportions that memory-retaining shape characteristics are imparted to said alloy.

12. The method as claimed in claim 10, wherein said force is less than approximately 1.6 pounds.

13. The method as claimed in claim 10, wherein said force is less than approximately 450 grams.

14. A method of expanding the distance between opposing molars of the mandibular or maxillary dental arch comprising the steps of:
spanning the interior cavity of a dental arch with an archwire composed of a temperature-affected material having a transition temperature below mouth temperature, said archwire having for its austenitic state configuration the orientation desired to be imparted to malaligned molars,
cooling said archwire to an martensitic state,
connecting said archwire to a lingual surface of each of two opposed molars,
permitting said archwire to achieve its austenitic state, and
exerting through the return of said archwire to its austenitic configuration a substantially continuous low-pressure force against said molars to provide corrective adjustments to said malaligned teeth and to expand the distance between opposing sides of the selected dental arch.

15. The method as claimed in claim 14 wherein said temperature-affected material is an alloy comprised of nickel and titanium in sufficient proportions that memory-retaining shape characteristics are imparted to said alloy.

16. The method as claimed in claim 14, wherein said force is less than approximately 1.6 pounds.

17. The method as claimed in claim 14, wherein said force is less than approximately 450 grams.

18. A method of uprighting, rotating and distalizing the molars of a dental arch comprising the steps of:
selecting an archwire composed of a temperature-affected material having a transition temperature below mouth temperature to a configuration to impart corrective uprighting, rotating and distalizing forces to malaligned molars as said archwire shifts from its martensitic state configuration to its austenitic state configuration,
attaching said archwire to the lingual surface of opposed malaligned molars, and
applying a substantially continuous low-pressure corrective force to said molars by said transition of said archwire from its martensitic state configuration to its austenitic state configuration to correct the malalignment.

19. The method as claimed in claim 18 wherein said temperature-affected material is an alloy comprised of nickel and titanium in sufficient proportions that memory-retaining shape characteristics are imparted to said alloy.

20. The method as claimed in claim 18 wherein said archwire is further comprised of an anterior vinyl pad for anchoring said archwire adjacent the incisors of the upper palate.

21. The method as claimed in claim 18, wherein said force is less than approximately 1.6 pounds.

22. The method as claimed in claims 18, wherein said force is less than approximately 450 grams.

23. An orthodontic archwire for expanding the maxillary palatal suture and repositioning teeth en masse using counter-force mechanics comprising:
at least one generally M-shaped archwire composed of a near-stoichiometric alloy of nickel and titanium having shape memory-retaining characteristics, said nickel-titanium alloy archwire following the palatal concavity bilaterally extending and terminating in a pair of ends, and
a pair of sheath inserts to receive said arch wire ends for connection of said ends to lingual sheaths on generally opposed molars such that a substantially continuous tooth-repositioning low force is applied to expand the palatal suture and reposition the teeth.

24. The method as claimed in claim 23, wherein said force is less than approximately 1.6 pounds.

25. The method as claimed in claim 23, wherein said force is less than approximately 450 grams.

26. The orthodontic archwire as claimed in claim 23 presenting a first archwire as an anteriorly extending loop segment and a second archwire as a posteriorly extending loop segment.

27. The orthodontic archwire as claimed in claim 23, wherein the inverse martensitic transformation of the nickel-titanium alloy terminates at a temperature below normal body temperature.

28. A method for uprighting, rotating, and distalizing molars and expanding the palatal arch between opposing molars in the mandibular or maxillary dental arch comprising:

step one: using an archwire composed of a temperature-affected material having a transition temperature below mouth temperature, step two: forming said archwire to present the configuration of a desired post-treatment palatal arch while said archwire is in its austenitic phase, step three: deforming the archwire while in its martensitic state to the configuration of a patient's pre-treated malaligned palatal arch, and step four: inserting the archwire into the patient's mouth and attaching the ends of the archwire into lingually projecting molar sheaths.

29. The method as claimed in claim 28, wherein said force is less than approximately 1.6 pounds.

30. The method as claimed in claim 28, wherein said force is less than approximately 450 grams.

* * * * *

UNITED STATES PATENT AND TRADEMARK OFFICE
CERTIFICATE OF CORRECTION

PATENT NO. : 5,399,087
DATED : March 21, 1995
INVENTOR(S) : Wendell V. Arndt

It is certified that error appears in the above-indentified patent and that said Letters Patent is hereby corrected as shown below:

Column 22, line 60, claim 24, after "The" delete "method" and insert --archwire-- therefor.

Column 22, line 62, claim 25, after "The" delete "method" and insert --archwire-- therefor.

Signed and Sealed this

Ninth Day of July, 1996

Attest:

BRUCE LEHMAN

*Attesting Officer*     *Commissioner of Patents and Trademarks*